United States Patent [19]

Thomas

[11] Patent Number: 4,857,321

[45] Date of Patent: Aug. 15, 1989

[54] SKIN OINTMENT

[76] Inventor: William C. Thomas, 8504 Punta Lora Dr., Pensacola, Fla. 32514

[21] Appl. No.: 240,064

[22] Filed: Aug. 26, 1988

[51] Int. Cl.$^4$ ............................................. A61K 35/12
[52] U.S. Cl. .................................. 424/95; 424/195.1; 514/858; 514/859; 514/863; 514/865; 514/873
[58] Field of Search .................. 424/95; 514/830, 858, 514/859, 863, 865, 873

[56] References Cited

U.S. PATENT DOCUMENTS

| | | | |
|---|---|---|---|
| 3,932,665 | 1/1976 | Van Scott et al. | 514/703 |
| 4,352,796 | 10/1982 | Arichi et al. | 514/825 |
| 4,389,418 | 6/1983 | Burton | 514/785 |
| 4,424,234 | 1/1984 | Alderson et al. | 514/784 |
| 4,459,285 | 7/1984 | Grollier et al. | 514/844 |
| 4,478,853 | 10/1984 | Chausser | 424/78 |
| 4,563,346 | 1/1986 | Deckner | 514/847 |
| 4,585,650 | 4/1986 | Newberry, Jr. et al. | 514/642 |
| 4,610,978 | 9/1986 | Dikstein et al. | 514/863 |
| 4,764,505 | 8/1988 | Fujinuma et al. | 514/25 |
| 4,769,234 | 9/1988 | Pines et al. | 424/63 |

*Primary Examiner*—Johnnie R. Brown
*Assistant Examiner*—Jean Witz
*Attorney, Agent, or Firm*—George A. Bode

[57] ABSTRACT

A skin ointment, comprising about twelve (12%) percent by volume mink oil; about nine (9%) percent by volume lanolin; about four (4%) percent by volume zinc stearate; about four (4%) percent by volume octylmethoxycinnamate; about four (4%) percent by volume methylgluceth—10; about four (4%) by volume peg 100 stearate; about three (3%) percent by volume cetal; about three (3%) percent by volume peanut oil; about two (2%) percent glyceral monostrearate; about two (2%) percent acetylated lanolin alcohol; about one (1%) percent spermaceti; about one (1%) percent propylene glycol; about one (1%) percent panthenol; less than one (1%) percent tocopheryl acetate; and, about forty-seven (47%) percent by volume water.

2 Claims, No Drawings

SKIN OINTMENT

BACKGROUND OF THE INVENTION

1. Field of the Invention

The present invention relates generally to an ointment for use on the skin, and more particularly to a skin ointment which is useful for softening facial wrinkles, moisturizing the skin, tightening the skin, and, soothing burns, psoriasis and athlete's foot, acne, baby diaper rash, bedsores and insect bites.

2. General Background

The most common uses of the ointment of the present invention disclosed herein is the softening of facial wrinkles, tightening the skin and the moisturizing of the skin. Other skin problems which are also in need of treatment are burns, psoriasis and athlete's foot which may lead the affected person to desire relief. Other skin problems which are treatable by the ointment disclosed herein are acne, baby diaper rash, bedsores and insect bites for which he present invention provides a soothing relief.

SUMMARY OF THE PRESENT INVENTION

It is a feature of the present invention to provide an ointment for use on the skin, and more particularly to a skin ointment which is useful for preventing wrinkles, moisturizing the skin, aid in the removal of moles, warts and corns, soothe burns, psoriasis and athletes foot. A semisolid water base is mixed with mink oil, lanolin, zinc stearate, octylmethoxycinnamate, methylgluceth—10, peg 100 stearate, cetal, peanut oil, glyceral monostrearate, acetylated lanolin alcohol, spermaceti, propylyene glycol, panthenol, tocopheryl acetate, retinol palmitate. Other ingredients included are aluminum sulfate, methyl paraben, ascorbal palmitate, E.D.T.A., propyl paraben, fragrance, tocopherol acetate and cholecalciferol. The preparation is normally applied as an ointment directly to the affected area. The preparation helps to lubricate and adds flexibility to the tissues.

DETAILED DESCRIPTION OF THE PREFERRED EMBODIMENT

In general, the preparation of the present invention utilizes active ingredients comprising mink oil, lanolin, zinc stearate, octylmethoxycinnamate, methylgluceth—10, peg 100 stearate, cetal, peanut oil, glyceral monostrearate, acetylated lanolin alcohol, spermaceti, propylene glycol, panthenol, tocopheryl acetate, retinol palmitate. Other ingredients included are aluminum sulfate, methyl paraben, ascorba palmitate, E.D.T.A.-(Ethylene Diamine Tetraacetic Acid), propyl paraben, fragrance, tocopherol acetate and A/D-3 (or cholecalciferol) which is mixed in a water base as a semisolid. The ointment is a semisolid at room and body temperature to provide for ease of application which is preferred due to ease of application. The preparation is normally applied to the affected area where the preparation may provide lubrication, promote healing, add flexibility to the affected tissues and serve as a protective layer against foreign material.

In preparing the ointment on a 100 parts by volume basis, 12 parts of mink oil, 2 parts of acetylated lanolin alcohol or acetulan, a trace amount—0.88 parts of tocopheryl acetate, 9.2 parts of deodorized lanolin in the form of ethoxylan 1685 (Solutan 75 may be substituted), 3.3 parts of cetal and a trace amount—0.1 part of ascorbal palmitate are mixed together to form a first mixture which is heated to seventy (70° C.) degrees centigrade for fifteen (15) minutes.

To the above mixture, 1.6 parts of spermaceti, 3.3 parts of Peg 100 Stearate, 4 parts of octylmethoxycinnamate, 2.2 parts of glycerol monostrearate, 4 parts of zinc stearate and a trace amount—0.1 parts of propyl paraben are blended. The temperature of this second mixture is then brought up to seventy (70° C.) degrees centigrade for thirty (30) minutes. As the second mixture is being blended, the water phase of the invention should be concurrently being prepared. Thus, 1 part of propylene glycol, 0.2 parts of methyl paraben, 0.5 parts of aluminum sulfate, 1 part of panthenol, 0.1 part of E.D.T.A. and 4 parts of methylgluceth—10 in the form of Glucam E-10 are mixed with 47.437 parts of water and heated to seventy (70° C.) degrees centigrade for thirty (30) minutes. After preparing the water phase, the water phase is blended with the previous or second mixture, thus forming a third mixture.

2.7 parts of peanut oil are now blended with the third mixture comprising the water phase and second mixture, and the admixed peanut oil and third mixture is removed from heat. This admixed peanut oil and third mixture is stirred until its cooled temperature has reached thirty five (35° C.) degrees centigrade. At this point, 0.458 parts of retinol palmitate, 0.05 parts of fragrance (such as rose geranium or mikko), 0.02 parts of tocopherol acetate and 0.055 parts of A/D-3 (or cholecalciferol) are blended with the admixed peanut oil and third mixture and the ointment is now ready for use.

In use, the ointment may be applied to the affected tissues where it may act as a protective dressing and a soothing emollient application to the skin while providing lubrication, adding flexibility to the affected tissue, and serving as a protective layer against foreign material.

Although the quantity of ingredients may be varied, the preferred embodiment of the preparation constitutes 12 parts of mink oil, 2 parts of acetylated lanolin alcohol, 0.88 parts of tocopheryl acetate, 9.2 parts of deodorized lanolin, 3.1 parts of cetal, 0.1 part of ascorbal palmitate, 1.6 parts of spermaceti, 3.3 parts of Peg 100 Stearate, 4 parts of octylmethoxycinnamate, 2.2 parts of glycerol monostrearate, 4 parts of zinc stearate, 0.1 parts of propyl paraben, 1 part of propylene glycol, 0.2 parts of methyl paraben, 0.5 parts of aluminum sulfate, 1 part of panthenol, 0.1 part of E.D.T.A., 4 parts of methylgluceth—10, 47.437 parts of water, 2.7 parts of peanut oil, 0.458 parts of retinol palmitate, 0.05 parts of fragrance, 0.02 parts of tocopherol acetate and 0.055 parts of A/D-3 (or cholecalciferol).

Because many varying and differing embodiments may be made within the scope of the inventive concept herein taught and because many modifications may be made in the embodiment herein detailed in accordance with the descriptive requirement of the law, it is to be understood that the details herein are to be interpreted as illustrative and not in a limiting sense.

What is claimed as invention is:

1. An ointment, comprising:
    (a) about twelve (12%) percent by volume mink oil;
    (b) about nine (9%) percent by volume lanolin;
    (c) about four (4%) percent by volume zinc stearate;
    (d) about four (4%) percent by volume octylmethoxycinnamate;
    (e) about four (4%) percent by volume methylgluceth—10;

(f) about four (4%) percent by volume peg 100 stearate;
(g) about three (3%) percent by volume cetal;
(h) about three (3%) percent by volume peanut oil;
(i) about two (2%) percent glyceral monostrearate;
(j) about two (2%) percent acetylated lanolin alcohol;
(k) about two (2%) percent spermaceti;
(l) about one (1%) percent propylene glycol;
(m) about one (1%) percent panthenol;
(n) about forty-seven (47%) percent by volume water;
(o) less than one (1%) percent tocopheryl acetate;
(p) less than one (1%) percent by volume retinol palmitate;
(q) less than one (1%) percent by volume aluminum sulfate;
(r) less than one (1%) percent by volume methyl paraben;
(s) less than one (1%) percent by volume ascorbal palmitate;
(t) less than one (1%) percent by volume E.D.T.A.;
(u) less than one (1%) percent by volume propyl paraben;
(v) less than one (1%) percent by volume tocopherol acetate;
(w) less than one (1%) percent by volume A/D-3;
(x) less than one (1%) percent by volume cholecalciferol; and,
(y) less than one (1%) percent by volume of a fragrance.

2. An ointment, comprising:
(a) about twelve (12%) percent by volume mink oil;
(b) about 9.2 percent by volume lanolin;
(c) about four (4%) percent by volume zinc stearate;
(d) about four (4%) percent by volume octylmethoxycinnamate;
(e) about four (4%) percent by volume methylgluceth—10;
(f) about 3.3 percent by volume peg 100 stearate;
(g) about 3.1 percent by volume cetal;
(h) about 2.7 percent peanut oil;
(i) about 2.2 percent glyceral monostrearate;
(j) about two (2%) percent acetylated lanolin alcohol;
(k) about 1.6 percent spermaceti;
(l) about one (1%) percent propylene glycol;
(m) about one (1%) percent panthenol;
(n) less than one (1%) percent tocopheryl acetate;
(o) about forty-seven (47%) percent by volume water;
(p) about 0.458 percent by volume retinol palmitate;
(g) about 0.5 percent by volume aluminum sulfate;
(r) about 0.2 percent by volume methyl paraben;
(s) about 0.1 percent by volume ascorbal palmitate;
(t) about 0.1 percent by volume E.D.T.A.;
(u) about 0.1 percent by volume propyl paraben;
(v) about 0.02 percent by volume tocopherol acetate; and,
(w) about 0.055 percent by volume A/D-3.

* * * * *